United States Patent
Lozier et al.

(10) Patent No.: US 8,979,935 B2
(45) Date of Patent: Mar. 17, 2015

(54) JOINT SPACE INTERPOSITIONAL PROSTHETIC DEVICE WITH INTERNAL BEARING SURFACES

(75) Inventors: Antony J. Lozier, Warsaw, IN (US); Russell M. Parrott, Warsaw, IN (US); David B. Rich, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 1332 days.

(21) Appl. No.: 12/179,707

(22) Filed: Jul. 25, 2008

(65) Prior Publication Data

US 2009/0036995 A1 Feb. 5, 2009

Related U.S. Application Data

(60) Provisional application No. 60/952,886, filed on Jul. 31, 2007.

(51) Int. Cl.
*A61F 2/30* (2006.01)
*A61B 17/00* (2006.01)
(Continued)

(52) U.S. Cl.
CPC ......... *A61F 2/30721* (2013.01); *A61F 2/30749* (2013.01); *A61B 17/00491* (2013.01); *A61B 17/06166* (2013.01); *A61B 17/68* (2013.01); *A61B 17/86* (2013.01); *A61F 2/30742* (2013.01); *A61F 2/30767* (2013.01); *A61F 2/30771* (2013.01); *A61F 2/30965* (2013.01); *A61F 2/32* (2013.01); *A61F 2/38* (2013.01); *A61F 2/3804* (2013.01); *A61F 2/40* (2013.01);
(Continued)

(58) Field of Classification Search
CPC ............ A61F 2002/30682; A61F 2002/30754; A61F 2002/30757; A61F 2002/3605; A61F 2/3603

USPC .......... 623/14.12, 16.11, 18.11, 19.13, 22.13, 623/23.11–23.14, 23.39–23.43, 23.5, 623/21.15–21.17, 22.18, 22.25
See application file for complete search history.

(56) References Cited

U.S. PATENT DOCUMENTS 1,448,111 A     3/1923   Eppler
3,855,638 A * 12/1974   Pilliar ........................ 623/23.55
(Continued)

FOREIGN PATENT DOCUMENTS

DE         1164019 B1    2/1964
DE         2015324 A1    11/1971
(Continued)

OTHER PUBLICATIONS

Translation of DE 10339605.*
(Continued)

*Primary Examiner* — Thomas J Sweet
*Assistant Examiner* — Megan Wolf
(74) *Attorney, Agent, or Firm* — Schwegman Lundberg & Woessner, P.A.

(57) ABSTRACT

Joint space interpositional prosthetic devices for positioning between surfaces of a joint in a patient are disclosed. The prosthetic device may have exterior surfaces affixed to the joint surfaces and may have internal surfaces which provide bearing surfaces. In an exemplary embodiment, the bearing surfaces are encapsulated within the device. The exterior surfaces of the device may include bone securement features to facilitate attachment of the prosthetic device to the joint surfaces.

27 Claims, 7 Drawing Sheets

(51) Int. Cl.

| | | |
|---|---|---|
| A61B 17/06 | (2006.01) | |
| A61B 17/68 | (2006.01) | |
| A61B 17/86 | (2006.01) | |
| A61F 2/32 | (2006.01) | |
| A61F 2/38 | (2006.01) | |
| A61F 2/40 | (2006.01) | |
| A61F 2/42 | (2006.01) | |
| A61F 2/28 | (2006.01) | |
| A61F 2/34 | (2006.01) | |
| A61F 2/46 | (2006.01) | |

(52) U.S. Cl.
CPC ............ *A61F 2/4202* (2013.01); *A61F 2/4241* (2013.01); *A61F 2/4261* (2013.01); *A61F 2002/2817* (2013.01); *A61F 2002/30004* (2013.01); *A61F 2002/30011* (2013.01); *A61F 2002/30065* (2013.01); *A61F 2002/302* (2013.01); *A61F 2002/30247* (2013.01); *A61F 2002/30364* (2013.01); *A61F 2002/30457* (2013.01); *A61F 2002/30461* (2013.01); *A61F 2002/30495* (2013.01); *A61F 2002/30596* (2013.01); *A61F 2002/30604* (2013.01); *A61F 2002/3064* (2013.01); *A61F 2002/30673* (2013.01); *A61F 2002/30677* (2013.01); *A61F 2002/30682* (2013.01); *A61F 2002/30688* (2013.01); *A61F 2002/30754* (2013.01); *A61F 2002/30757* (2013.01); *A61F 2002/30957* (2013.01); *A61F 2002/30971* (2013.01); *A61F 2002/30981* (2013.01); *A61F 2002/3474* (2013.01); *A61F 2002/4631* (2013.01); *A61F 2002/4635* (2013.01); *A61F 2210/0071* (2013.01); *A61F 2220/0025* (2013.01); *A61F 2220/0033* (2013.01); *A61F 2220/0058* (2013.01); *A61F 2220/0075* (2013.01); *A61F 2230/0065* (2013.01); *A61F 2230/0071* (2013.01); *A61F 2250/0014* (2013.01); *A61F 2250/0023* (2013.01); *A61F 2310/00023* (2013.01); *A61F 2310/00029* (2013.01); *A61F 2310/00161* (2013.01); *A61F 2310/00203* (2013.01); *A61F 2310/00239* (2013.01); *A61F 2310/00329* (2013.01); *A61F 2310/00491* (2013.01); *A61F 2310/00544* (2013.01)
USPC .................. 623/18.11; 623/14.12; 623/23.12; 623/23.42

(56) References Cited

U.S. PATENT DOCUMENTS

| | | | |
|---|---|---|---|
| 4,312,079 A | 1/1982 | Dorre et al. | |
| 4,355,429 A | 10/1982 | Mittelmeier et al. | |
| 4,467,479 A | 8/1984 | Brody | |
| 4,502,161 A | 3/1985 | Wall | |
| 4,769,039 A | 9/1988 | Horber | |
| 4,839,215 A | 6/1989 | Starling et al. | |
| 4,896,663 A | 1/1990 | Vandewalls | |
| 4,932,969 A | 6/1990 | Frey et al. | |
| 4,966,924 A | 10/1990 | Hyon et al. | |
| 4,976,740 A | 12/1990 | Kleiner | |
| 5,041,138 A | 8/1991 | Vacanti et al. | |
| 5,080,678 A | 1/1992 | Spotorno et al. | |
| 5,147,904 A | 9/1992 | Jochum et al. | |
| 5,217,498 A | 6/1993 | Henssge et al. | |
| 5,246,459 A | 9/1993 | Elias | |
| 5,271,737 A | 12/1993 | Baldwin et al. | |
| 5,282,861 A | 2/1994 | Kaplan | |
| 5,312,409 A | 5/1994 | McLaughlin et al. | |
| 5,314,478 A | 5/1994 | Oka et al. | |
| 5,358,525 A | 10/1994 | Fox et al. | |
| 5,370,700 A | 12/1994 | Sarkisian et al. | |
| 5,458,643 A | 10/1995 | Oka et al. | |
| 5,553,476 A | 9/1996 | Oehy et al. | |
| 5,556,429 A | 9/1996 | Felt | |
| 5,607,474 A | 3/1997 | Athanasiou et al. | |
| 5,609,641 A | 3/1997 | Johnson et al. | |
| 5,609,646 A | 3/1997 | Field et al. | |
| 5,645,592 A | 7/1997 | Nicolais et al. | |
| 5,658,343 A | 8/1997 | Hauselmann et al. | |
| 5,795,353 A | 8/1998 | Felt | |
| 5,817,098 A | 10/1998 | Albrektsson et al. | |
| 5,871,541 A | 2/1999 | Gerber | |
| 5,951,564 A | 9/1999 | Schroder et al. | |
| 6,113,640 A * | 9/2000 | Tormala et al. | ............ 623/18.11 |
| 6,132,468 A | 10/2000 | Mansmann | |
| 6,140,452 A | 10/2000 | Felt et al. | |
| 6,168,630 B1 | 1/2001 | Keller et al. | |
| 6,224,630 B1 | 5/2001 | Bao et al. | |
| 6,231,605 B1 | 5/2001 | Ku | |
| RE37,277 E | 7/2001 | Baldwin et al. | |
| 6,306,177 B1 | 10/2001 | Felt et al. | |
| 6,425,923 B1 | 7/2002 | Stalcup et al. | |
| 6,443,988 B2 | 9/2002 | Felt et al. | |
| 6,447,514 B1 | 9/2002 | Stalcup et al. | |
| 6,494,917 B1 | 12/2002 | McKellop et al. | |
| 6,530,956 B1 | 3/2003 | Mansmann | |
| 6,533,818 B1 | 3/2003 | Weber et al. | |
| 6,547,828 B2 | 4/2003 | Scott et al. | |
| 6,620,196 B1 | 9/2003 | Trieu | |
| 6,629,997 B2 | 10/2003 | Mansmann | |
| 6,652,587 B2 | 11/2003 | Felt et al. | |
| 6,652,588 B2 | 11/2003 | Hayes, Jr. et al. | |
| 6,679,913 B2 | 1/2004 | Homsy | |
| 6,719,797 B1 | 4/2004 | Ferree | |
| 6,827,743 B2 | 12/2004 | Eisermann | |
| 6,994,730 B2 | 2/2006 | Posner | |
| 7,001,431 B2 | 2/2006 | Bao et al. | |
| 7,077,865 B2 | 7/2006 | Bao et al. | |
| 7,291,169 B2 | 11/2007 | Hodorek | |
| 7,462,180 B2 | 12/2008 | Raugel et al. | |
| 2001/0033857 A1 | 10/2001 | Vyakarnam et al. | |
| 2001/0039455 A1 | 11/2001 | Simon et al. | |
| 2002/0022884 A1 | 2/2002 | Mansmann | |
| 2002/0029083 A1 | 3/2002 | Zucherman et al. | |
| 2002/0127264 A1 | 9/2002 | Felt et al. | |
| 2002/0128715 A1 * | 9/2002 | Bryan et al. | ............... 623/17.15 |
| 2002/0156531 A1 | 10/2002 | Felt et al. | |
| 2002/0161448 A1 | 10/2002 | Hayes, Jr. et al. | |
| 2002/0173852 A1 | 11/2002 | Felt et al. | |
| 2002/0173855 A1 | 11/2002 | Mansmann | |
| 2002/0183845 A1 | 12/2002 | Mansmann | |
| 2002/0183850 A1 | 12/2002 | Felt et al. | |
| 2002/0188300 A1 | 12/2002 | Arramon et al. | |
| 2002/0193883 A1 | 12/2002 | Wironen | |
| 2003/0008396 A1 | 1/2003 | Ku | |
| 2003/0074076 A1 | 4/2003 | Ferree et al. | |
| 2003/0078617 A1 | 4/2003 | Schwartz et al. | |
| 2003/0130741 A1 | 7/2003 | McMinn | |
| 2003/0153918 A1 | 8/2003 | Putnam et al. | |
| 2003/0163202 A1 | 8/2003 | Lakin | |
| 2003/0195628 A1 | 10/2003 | Bao et al. | |
| 2003/0220649 A1 | 11/2003 | Bao et al. | |
| 2003/0225457 A1 * | 12/2003 | Justin et al. | ............... 623/20.14 |
| 2004/0010312 A1 | 1/2004 | Enayati | |
| 2004/0039447 A1 | 2/2004 | Simon et al. | |
| 2004/0051213 A1 | 3/2004 | Muratoglu | |
| 2004/0107000 A1 | 6/2004 | Felt et al. | |
| 2004/0133275 A1 | 7/2004 | Mansmann | |
| 2004/0138754 A1 | 7/2004 | Lang et al. | |
| 2004/0153163 A1 | 8/2004 | Posner | |
| 2004/0163681 A1 | 8/2004 | Verhaverbeke | |
| 2004/0199250 A1 | 10/2004 | Fell | |
| 2004/0220582 A1 | 11/2004 | Keller | |
| 2004/0236424 A1 | 11/2004 | Berez et al. | |
| 2004/0247641 A1 | 12/2004 | Felt et al. | |
| 2004/0267371 A1 | 12/2004 | Hayes, Jr. et al. | |
| 2005/0021042 A1 | 1/2005 | Marnay et al. | |
| 2005/0043808 A1 | 2/2005 | Felt et al. | |
| 2005/0075642 A1 | 4/2005 | Felt et al. | |

(56) References Cited

U.S. PATENT DOCUMENTS

| | | |
|---|---|---|
| 2005/0125077 A1 | 6/2005 | Harmon et al. |
| 2005/0171604 A1 | 8/2005 | Michalow |
| 2005/0251149 A1 | 11/2005 | Wenz |
| 2005/0251266 A1 | 11/2005 | Maspero et al. |
| 2005/0287187 A1 | 12/2005 | Mansmann |
| 2006/0009853 A1 | 1/2006 | Justin et al. |
| 2006/0079905 A1 | 4/2006 | Beyar et al. |
| 2006/0085080 A1 | 4/2006 | Bechgaard et al. |
| 2006/0149389 A1 | 7/2006 | Romagnoli |
| 2006/0224244 A1 | 10/2006 | Thomas et al. |
| 2006/0235542 A1 | 10/2006 | Hodorek et al. |
| 2006/0253200 A1 | 11/2006 | Bao et al. |
| 2007/0027230 A1 | 2/2007 | Beyar et al. |
| 2007/0038300 A1 | 2/2007 | Bao et al. |
| 2007/0088444 A1 | 4/2007 | Hodorek et al. |
| 2007/0142916 A1 | 6/2007 | Olson et al. |
| 2007/0179607 A1 | 8/2007 | Hodorek et al. |
| 2007/0224238 A1 | 9/2007 | Mansmann et al. |
| 2008/0051889 A1 | 2/2008 | Hodorek |
| 2008/0071381 A1* | 3/2008 | Buscher et al. ............ 623/18.11 |
| 2008/0215057 A1 | 9/2008 | Willi |
| 2008/0221700 A1 | 9/2008 | Howald |

FOREIGN PATENT DOCUMENTS

| | | |
|---|---|---|
| DE | 2501080 A1 | 7/1976 |
| DE | 2933174 A1 | 4/1980 |
| DE | 2953575 A1 | 7/1982 |
| DE | 3923418 A1 | 1/1991 |
| DE | 4317448 A1 | 11/1994 |
| DE | 29513894 U1 | 11/1995 |
| DE | 19721661 A1 | 11/1998 |
| DE | 19803183 A1 | 8/1999 |
| DE | 10021387 A1 | 11/2001 |
| DE | 20303205 U1 | 4/2003 |
| DE | 10220368 A1 | 12/2003 |
| DE | 10339605 A1 | 4/2005 |
| EP | 0013863 A1 | 8/1980 |
| EP | 0013864 A1 | 8/1980 |
| EP | 0017930 A1 | 10/1980 |
| EP | 0170779 A1 | 2/1986 |
| EP | 0528080 A1 | 2/1993 |
| EP | 0480954 B1 | 4/1993 |
| EP | 0552949 A1 | 7/1993 |
| EP | 0577529 A1 | 1/1994 |
| EP | 0639356 A1 | 2/1995 |
| EP | 0768066 A2 | 4/1997 |
| EP | 0892627 B1 | 1/1999 |
| EP | 0992222 A2 | 4/2000 |
| EP | 0507645 B1 | 7/2001 |
| EP | 1340477 A2 | 9/2003 |
| EP | 1407728 A1 | 4/2004 |
| EP | 1477120 A1 | 11/2004 |
| EP | 1588669 A1 | 10/2005 |
| FR | 2519545 A1 | 7/1983 |
| FR | 2691355 A1 | 11/1993 |
| FR | 2692140 A1 | 12/1993 |
| FR | 2803190 A1 | 7/2001 |
| FR | 2803191 A1 | 7/2001 |
| GB | 1126961 | 11/1968 |
| GB | 1349987 A | 4/1974 |
| GB | 2139097 A | 11/1984 |
| WO | WO97/37613 A1 | 10/1997 |
| WO | WO00/15153 A1 | 3/2000 |
| WO | WO00/23009 A1 | 4/2000 |
| WO | WO01/45595 A2 | 6/2001 |
| WO | WO02/41808 A1 | 5/2002 |
| WO | WO02/054992 A | 7/2002 |
| WO | WO2004/032987 A | 4/2004 |
| WO | WO2005/051242 A1 | 6/2005 |
| WO | WO2006/060555 A1 | 6/2006 |
| WO | WO2007/054553 A1 | 5/2007 |
| WO | WO2007/090790 A2 | 8/2007 |
| WO | WO2007/125060 A1 | 11/2007 |

OTHER PUBLICATIONS

Definition of "concentric'" from the Merriam-Webster online dictionary, accessed Mar. 14, 2011.*

Quinton, J.S. and P.C. Dastoor, "Characterizing the bonding mechanisms at silane-metal interfaces: a model system", J. Mat. Sci. Letters, vol. 18, Nov. 1999, pp. 1833-1835.

The International Preliminary Report on Patentability mailed Feb. 11, 2010 from the International Bureau in related International Patent Application No. PCT/US2008/071141.

Office Action mailed Jul. 8, 2010 in U.S. Appl. No. 12/278,835.

Response filed Oct. 1, 2010 in U.S. Appl. No. 12/278,835.

International Preliminary Report on Patentability mailed Sep. 9, 2008 in International Application No. PCT/EP2007/051008.

* cited by examiner

JOINT SPACE INTERPOSITIONAL PROSTHETIC DEVICE WITH INTERNAL BEARING SURFACES

CROSS-REFERENCE TO RELATED APPLICATIONS

The present application claims the benefit of U.S. Provisional Patent Application No. 60/952,886 filed Jul. 31, 2007, titled JOINT SPACE INTERPOSITIONAL PROSTHETIC DEVICE WITH INTERNAL BEARING SURFACES, the entire disclosure of which is expressly incorporated herein by reference.

FIELD OF THE DISCLOSURE

The present disclosure relates to joint interposition arthroplasty. More particularly, the present disclosure relates to surgical methods and prostheses for joint interposition arthroplasty.

BACKGROUND

Joint interposition arthroplasty involves a surgical procedure to repair a joint in a patient. Damage and imperfections in joint surfaces, whether caused by wear, trauma or disease, may cause pain or discomfort to the patient during joint articulation. Implants which may be used in joint interposition arthroplasty to repair the joint, particularly when implantation can be achieved without full distraction of the joint, may be desirable to reduce the impact of the procedure on the patient and to reduce recovery time.

SUMMARY

The present disclosure provides joint space interpositional prosthetic devices. In an exemplary disclosed embodiment, the prosthetic device comprises a first prosthetic component coupled to a second prosthetic component. The first and second prosthetic components are sized and shaped for positioning over natural articular surfaces associated with a joint in a patient. The first prosthetic component includes a first external region having a first bone securement feature and a first internal region having a first articulation surface. The second prosthetic component includes a second external region having a second bone securement feature and a second internal region having a second articulation surface. The first internal region and the second internal region form an encapsulated body for containing debris produced from articulation between the first interior region and the second interior region.

In another exemplary disclosed embodiment, the prosthetic device comprises a first prosthetic component and a second prosthetic component. The first and second prosthetic components are sized and shaped for positioning over natural articular surfaces associated with the joint in a patient. The first prosthetic component includes a first securement means for securing the first prosthetic component to the first joint surface, and the second prosthetic component includes a second securement means for securing the second prosthetic component to the second joint surface. The prosthetic device also includes containment means for containing debris produced from articulation between said first prosthetic component and said second prosthetic component.

A method of enhancing articulation between a first joint surface and a second joint surface is also disclosed. An exemplary disclosed embodiment of the method includes the steps of providing a prosthetic device, partially distracting the joint, deforming the prosthetic device, and affixing the prosthetic device to the first and second joint surfaces. The device comprises flexible first and second prosthetic components. The prosthetic components are sized and shaped for positioning over natural articular surfaces associated with a joint in a patient. The flexible prosthetic components include internal regions and bone securement features. The internal regions have bearing surfaces. The first internal region and the second internal region form an encapsulated body for containing debris produced from articulation between the first bearing surface and the second bearing surface. The prosthetic device is deformed while positioning the prosthetic device between the first joint surface and the second joint surface of the partially distracted joint. The first and second prosthetic components are sufficiently flexible to allow the prosthetic device to be positioned between the first joint surface and the second joint surface with the joint only partially distracted.

In a further exemplary disclosed embodiment, the prosthetic device comprises a first prosthetic component and a second prosthetic component. The first and second prosthetic components are sized and shaped for positioning over natural articular surfaces associated with a joint in a patient. The first prosthetic component includes a first external region having a first bone securement feature and a first internal region having a first articulation surface. The second prosthetic component includes a second external region having a second bone securement feature and a second internal region having a second articulation surface. The first bone securement feature is affixed to less than all of the natural articular surface associated with the first joint surface.

BRIEF DESCRIPTION OF THE DRAWINGS

The above-mentioned and other features of the invention, and the manner of attaining them, will become more apparent and will be better understood by reference to the following description of disclosed embodiments taken in conjunction with the accompanying drawings, wherein.

Corresponding reference characters indicate corresponding parts throughout the several views. Although the drawings represent embodiments of the present invention, the drawings are not necessarily to scale and certain features may be exaggerated to better illustrate and explain the present invention. The exemplifications set out herein illustrate embodiments of the disclosure and such exemplifications are not to be construed as limiting the scope of the invention in any manner.

DETAILED DESCRIPTION

The embodiments discussed below are not intended to be exhaustive or limit the invention to the precise forms disclosed in the following detailed description. Rather, the embodiments are chosen and described so that others skilled in the art may utilize their teachings.

Figure 1:
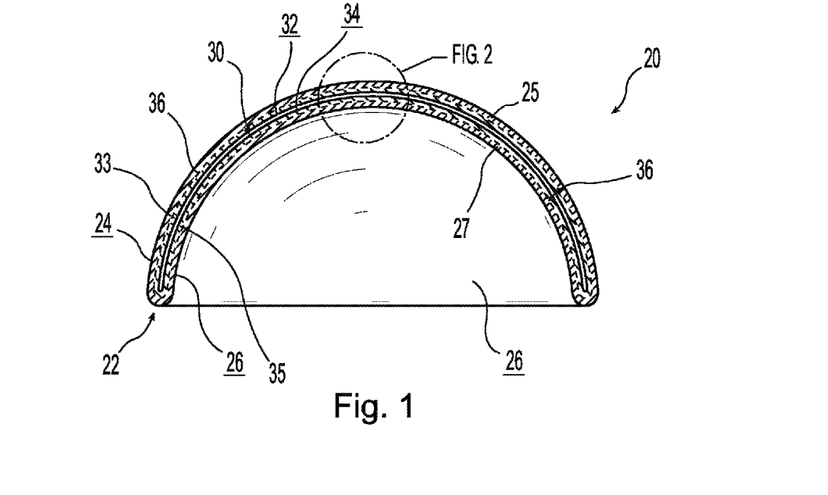
FIG. 1 is a cross-sectional view of an exemplary joint interpositional device.
Figure 2:
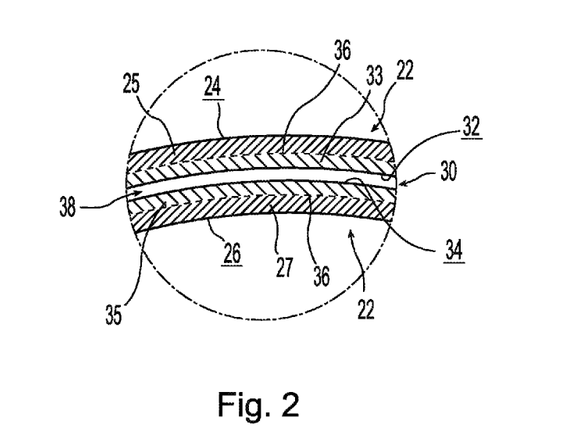
FIG. 2 is a fragmentary cross-sectional view of a portion of the joint interpositional device of FIG. 1.

Referring now to FIGS. 1 and 2, an exemplary joint interpositional device 20 is shown. Device 20 generally may include exterior portion 22 and interior or internal portion 30. In operation, device 20 is positioned between a first joint surface and a second joint surface, as described below with reference to FIG. 3. In an exemplary embodiment, as shown in FIG. 1, device 20 is formed as a hemispherically-shaped structure, half of which is illustrated in FIG. 1, which is sized and shaped to be positioned over, and conform to, natural articular surfaces of an anatomical structure. In one example, device 20 may be formed as a spherical device with exterior portion 22 forming the exterior of the sphere, after which device 20 is partially inverted to form a hemisphere shape, as shown in FIG. 1.

Exterior portion 22 defines first exterior region 25 having first exterior surface 24 and second exterior region 27 having second exterior surface 26. In one embodiment, first exterior region 25 and second exterior region 27 are formed of the same material and exterior portion 22 has a continuous cross-section between first exterior surface 24 and second exterior surface 26. A continuous cross-section is formed or composed of material without joints or seams. By contrast, a discontinuous cross-section has joints or seams.

Exterior regions 25, 27 may have thicknesses T ranging between about 0.25 and 3.00 mm. In another embodiment, exterior regions 25, 27 may have thicknesses ranging between about 0.50 and 1.50 mm. Exterior regions 25, 27 may be formed of various materials comprising bone securement features for attaching exterior regions 25, 27 to bones, bone cartilage, or other anatomical structures. For example, exterior regions 25, 27 may be formed of a polyethylene material, other polymer materials such as polytetrafluoroethylene (PTFE), a rubberized material, or other biocompatible materials. In another exemplary embodiment, exterior regions 25, 27 are formed in a fibrous construct including any or all of the above-identified materials. Exemplary fibrous constructs include nonwovens and also braided, knitted and woven structures.

Interior portion 30 defines first interior region 33 having first interior surface 32 and second interior region 35 having second interior surface 34. Similar to exterior surfaces 24, 26, described above, first interior region 33 and second interior region 35 may be formed of the same material and interior portion 30 may have a continuous cross-section between first interior surface 32 and second interior surface 34. Interior regions 33, 35 may be formed of various materials which facilitate articulation between interior surfaces 32, 34. For example, interior regions 33, 35 may be formed of synthetic polymers (i.e. ultra high molecular weight polyethylene (UHMWPE), polyether-ether-ketone (PEEK), polyether-ketone (PEK)), ceramics/glass (i.e. Alumina, Zirconia, Pyrolytic Carbon), metals (i.e. Titanium, Cobalt Chrome Alloy), or a composite of these materials (Carbon Reinforced PEEK). In one embodiment, interior regions 33, 35 are formed into a fibrous construct including any or all of the above-identified materials. In an exemplary embodiment, interior regions 33, 35 may include a lubrication-enhancement material such as a polysaccharide, protein, or synthetic coating embedded therein or a surface treatment applied to interior surfaces 32, 34 to enhance the lubrication between surfaces 32, 34 in use. Alternatively, gap 38 (FIG. 2) between interior surfaces 32, 34 may be filled with a biocompatible lubricant such as hyaluronic acid.

The interior and exterior regions of the implant may be porous. The stimulatory effect of polyethylene particles in vitro decreases when the largest dimension of particles is larger than about 7.0 micrometers (µm) or smaller than about 0.2 µm. The polyethylene wear particles commonly found in hip arthroplasties have a diameter of about 0.5 µm. Interior regions 33, 35 may be configured reduce the stimulatory effect of the implant by containing wear particles in one or more ways. In one embodiment designed to contain wear particles, the average pore size of interior regions 33, 35 is smaller than the average pore size of exterior regions 25, 27. In another embodiment, interior surfaces 32, 34 and/or exterior surfaces 24, 26 may include a coating or other containment facilitation device to contain wear particles generated from within device 20. An example of a device to contain particles includes a prosthetic hip joint with a semipermeable capsule with reinforcing ribs as disclosed in U.S. Pat. No. 5,514,182. This device proposes the use of expanded polytetrafluoroethylene (ePTFE) marketed by W. L. Gore & Associates of Newark, Del. under the trademark GORE-TEX. In a further embodiment, the average pore size of interior regions 33, 35 may be less than about 0.2 µm. In yet another embodiment, exterior regions 25, 27 may have an average pore size of less than about 0.2 µm. In some embodiments, exterior regions 25, 27 may have average pore sizes of between 100 µm and 700 µm.

Transition 36 may be provided between first interior region 33 and first exterior region 25 as well as between second interior region 35 and second exterior region 27. Transition 36 defines a transition area between interior regions 33, 35 and exterior regions 25, 27 which may include a change of interior and exterior region materials. For example, interior regions 33, 35 may be formed of a material which is designed to provide enhanced lubrication and/or abrasion resistance, such as polyethylene, PTFE, PEEK, silicone, or nylon, while exterior regions 25, 27 may be formed of material designed to enhance fixation to an anatomical structure such as, for example, a porous polymer or a fibrous construct. In one embodiment, transition 36 defines the transition between layers of material formed into interior regions 33, 35 and exterior regions 25, 27.

In an exemplary embodiment, joint interpositional device 20 is a unitary construct. For example, device 20 may be formed in an injection molding process, a blow molding process, or an extrusion process. A unitary construct may include two or more layers of materials which may be the same or may be different. In an injection molding mold, molten materials flow in the mold cavity and come together to form a unitary construct. Because molds may comprise two mating parts, a line or mark may appear on an injection molded article in the area coincident with the seam of the mold. Such lines or marks, which may be visible on the surface of an article, do not form cross-sectional discontinuities since the molten materials fuse before solidifying and, therefore, do not exhibit seams or joints in their cross-section. In one example, device 20 may be formed as a spherical device with exterior portion 22 forming the exterior of the sphere, after which device 20 is partially inverted to form a hemisphere shape, as shown in FIG. 1. In other embodiment disclosed with reference to FIGS. 4-8, the joint interpositional device is formed from multiple pieces of material. A multi-piece construct may have a discontinuous cross-section in its external and/or internal regions.

Joint interpositional device 20 may include an internal rotation device, such as a rotating ring or ball bearing-type device, to facilitate articulation between a first joint surface and a second joint surface while preventing relative motion between exterior portion 22 of device 20 and the joint surfaces. An exemplary embodiment of an internal rotation device is described below with reference to FIGS. 6-8.

Figure 3:
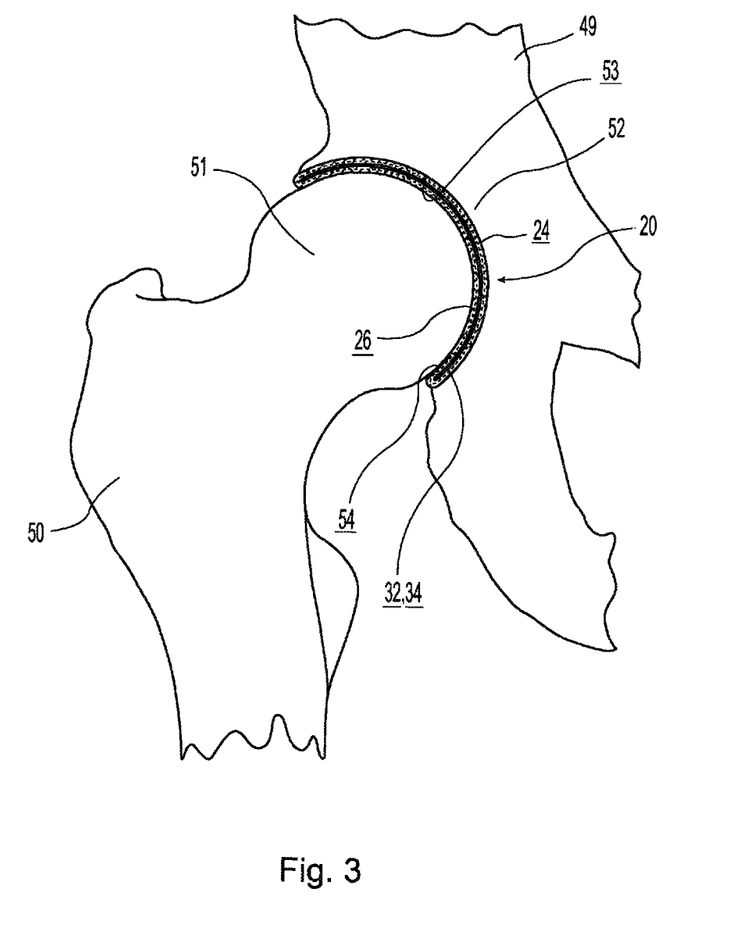
FIG. 3 is an anterior view of a femur and an acetabulum showing a cross-sectional view of the joint interpositional device of FIG. 1 positioned between the femur and the acetabulum.

Referring to FIG. 3, in an exemplary method, joint interpositional device 20 may be positioned between femoral head 51 of femur 50 and acetabulum 52 of pelvis 49 without fully distracting the joint. The articular region of femoral head 51 defines femoral head surface 54 and the articular region of acetabulum 52 defines acetabulum surface 53. To insert device 20, femoral head 51 is partially and, preferably, minimally distracted from acetabulum 52 and device 20 is slid between femoral head surface 54 and acetabulum surface 53. Partial distraction, in the context of a joint formed by femoral head 51 and acetabulum 52, means less than full distraction, i.e., less than complete removal of femoral head 51 from acetabulum 52. With partial distraction, some portion of femoral head 51 will remain within the acetabulum below the acetabular rim. Partial distraction can occur when the joint is distracted less than about 36.0 mm.

Femoral head 51 and/or acetabulum 52 may be prepared to receive device 20. Preparation may include removing portions of the natural articulating surfaces, for example, without resecting the bone or fully distracting the joint. Device 20 may be used with an arthritic joint and, thus, may be used to substantially preserve the existing bone stock of the joint without requiring extensive modification of the natural articular surfaces of the joint. In an exemplary operation, device 20 is large enough to cover the articular region of femoral head 51 which contacts acetabulum 52 during hip joint articulation. Although described herein as used with a hip joint, device 20 may also be used in other joints of the body, such as a knee, elbow, shoulder, wrist, finger, and ankle joints, for example.

Device 20 may be flexible to enable insertion in a partially distracted joint. Device 20 may be constructed of flexible, elastic or other materials which may conform to any irregularities present on the surface of femoral head 51 and/or acetabulum 52. An elastic material is a material having a shape which may be elastically or reversibly deformed by the temporary application of force. Upon removal of the temporary force, the elastic material regains substantially its original shape suffering no more than about 15% permanent deformation or set. The applied force may be tensile, compressive or shear force. A flexible material, by contrast, may be temporarily deformed by the application of force but will not automatically regain substantially its original shape when the force is removed. Another force may be applied to cause the material to regain its original shape. In other words, the shape of a flexible material may be changed without causing permanent deformation. By using at least some elastic or flexible materials, device 20 may be made flexible and may be positioned into the partially distracted joint by the application of force which causes device 20 to change its shape without permanently deforming its shape or impeding its function as a result of the application of said force. Furthermore, elasticity and flexibility in portions of device 20 that are not affixed to natural articulating surfaces enable an affixed portion of device 20 to articulate in three dimensions relative to the other affixed portion by stretching or allowing the edges of the device to roll onto themselves. During articulation, the elastic or flexible portions may recede away from the natural articulating surfaces which may become exposed.

First exterior surface 24 is affixed to acetabulum surface 53 and second exterior surface 26 is affixed to femoral head surface 54. In embodiments of devices having continuous cross-sections, for example device 20 shown in FIGS. 1-3, affixation may be completed with adhesives, bio-adhesives, suturing, micro-fixation, bone cement, hook-and-loop arrangements, and various other known structures for securing a foreign body to an anatomical structure. In other embodiments, for example multi-piece devices such as devices 60, 100 and 200 shown in FIGS. 4-8, affixation may be completed with adhesives, bio-adhesives, suturing, micro-fixation, bone cement, hook-and-loop arrangements, fasteners including screws and nails, and various other known materials and structures for securing a foreign body to an anatomical structure.

Figure 4:
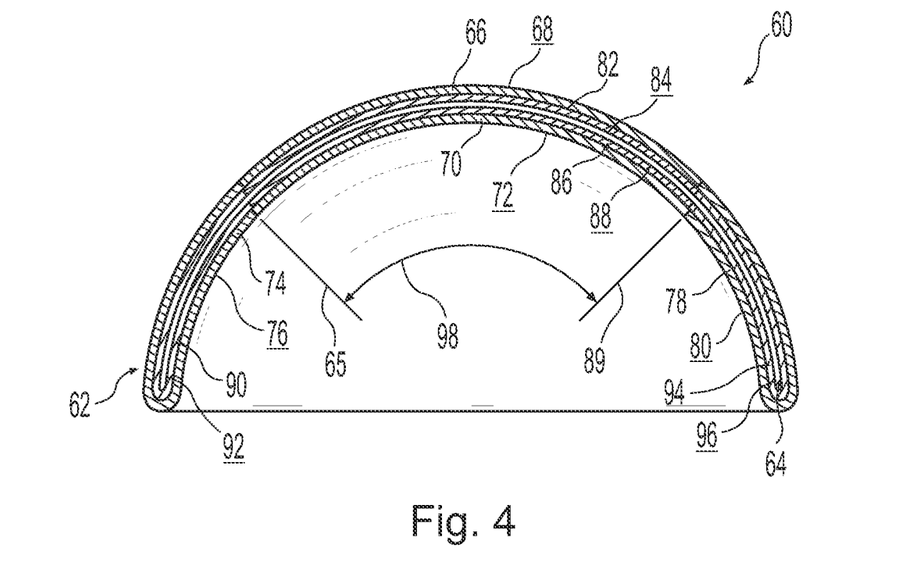
FIGS. 4-5 are partial cross-sectional views of additional exemplary joint interpositional devices.
Figure 5:
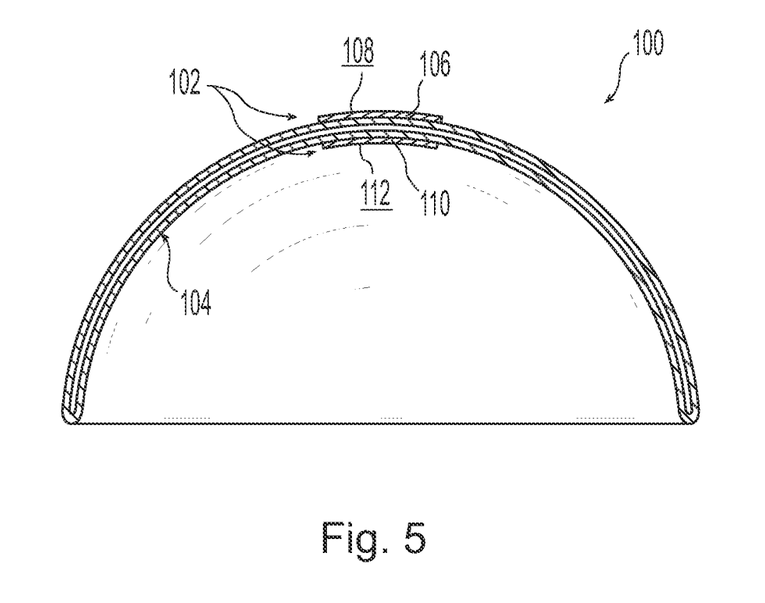

In exemplary embodiments shown in FIGS. 4-5, exterior surfaces 24, 26 may textured to provide a bone securement feature. By textured it is meant a surface having a surface roughness sufficient to enable tissue to embed therein. By tissue it is meant any group of cells or native organic materials that perform specific functions, e.g., bone, calcified organic materials, and frameworks of fibers that support other tissues. A textured surface may enable ongrowth of tissue compared to porous surface which may provide for both or either tissue ingrowth and ongrowth. A textured bone securement feature may also be provided by a cellular structure which resembles bone and approximates the physical and mechanical properties of bone, thereby enabling rapid and extensive soft tissue infiltration and strong attachment of bone and soft tissue structures thereto. The cellular material may be a highly porous biomaterial having a porosity as low as 55, 65, or 75 percent or as high as 80, 85, or 90 percent. An example of such a material is produced using Trabecular Metal™ technology generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the disclosure of which is expressly incorporated herein by reference. In addition to tantalum, other metals such as niobium, or alloys of tantalum and niobium with one another or with other metals may also be used.

In another example of a bone securement feature, exterior surface 24, 26 may include tissue ingrowth material or bone growth factors embedded therein, such as bone morphogenic proteins to stimulate bone growth. Exterior surface 24, 26 may also include bone growth stimulators, antibiotics, and other pharmacological and/or therapeutic agents. The exterior portions of joint interpositional devices disclosed herein may be attached to the interior portions by any means known in the art such as, for example, chemical bonding, physical or mechanical attachment, ultrasonic bonding, sewing, and others.

During articulation between femoral head 51 and acetabulum 52, first interior or internal bearing surface 32 and second interior or internal bearing surface 34 move relative to each other and first exterior surface 24 and second exterior surface 26 remain substantially stationary relative to femoral head 51 and acetabulum 52 to which they are affixed. At least portions of exterior surface 24 and exterior surface 26 may slightly move relative to femoral head 51 and acetabulum 52 during certain joint articulations, such as abduction. As shown in FIG. 3, during use, surfaces 32, 34 are virtually coincident due to the weight-bearing between acetabulum 52 and femoral head 51, thereby substantially eliminating the presence of gap 38 between surfaces 32, 34 and forcing any lubricant contained in gap 38 to substantially cover surfaces 32, 34 to provide lubrication therebetween. Internal bearing surfaces 32, 34 provide the articulation surfaces between femoral head 51 and acetabulum 52. As shown in FIGS. 1, 4 and 5, each of interior portion 30 of device 20, internal portion 64 of device 60, and internal portion 104 of device 100 forms an encapsulated body where wear debris or other material generated during articulation may be contained thereby reducing the likelihood of damage to surrounding regions of tissue or bone by the presence of wear debris. In another embodiment, first exterior surface 24 and second exterior surface 26 may form a continuous surface which creates an encapsulated body where debris may be contained. A continuous surface is a surface without breaks, separations, apertures, gaps or other discontinuities which may permit wear debris to pass through the surface. Moreover, fluid film lubrication schemes between internal bearing surfaces 32, 34 may eliminate direct articulation between femoral head surface 54 and acetabulum surface 53, thereby eliminating any wear debris therebetween to facilitate prevention of device 20 loosening, preserving the existing bone stock for an extended period of time, and potentially reducing pain during movement of femoral head 51 relative to acetabulum 52.

If, for any reason, device 20 needs to be removed after implantation, device 20 may be replaced with a new device 20 which is subsequently affixed to femoral head surface 54 and acetabulum surface 53, as described above.

Referring now to FIG. 4, another exemplary joint interpositional device is shown. Device 60 generally may include exterior portion 62 and interior or internal portion 64. In operation, device 60 is positioned between a first joint surface and a second joint surface and functions similarly to device 20, as described above with reference to FIG. 3. Exterior portion 62 includes a first exterior region 66, a second exterior region 70, and exterior regions 74 and 78 connecting exterior regions 66 and 70. First exterior region 66 has a first exterior surface 68, second exterior region 70 has a second exterior surface 72, and exterior regions 74 and 78 have exterior surfaces 76 and 80 connecting first and second exterior surfaces 68 and 72, respectively. Device 60 is a multi-piece construction. First and second exterior region 66, 70 are generally delimited by lines numbered 65 and 89 and their cross-sections shown extend in a direction parallel to line 98. First exterior region 66 may comprise a surface area smaller than the surface area of acetabulum surface 53, and second exterior region 70 may comprise a surface area smaller than the surface area of the articulating surface of femoral head surface 54. In another embodiment, first exterior region 66 comprises a surface area smaller than about 50% of the surface area of acetabulum surface 53, and second exterior region 70 comprises a surface area smaller than about 50% of the surface area of the articulating surface of femoral head surface 54. Exterior region 74, 80 may form seams with first and second exterior region 66, 70. In one embodiment, first exterior region 66 and second exterior region 70 are formed of the same material and exterior regions 74 and 78 are made of a material different from that of which first and second exterior regions 66 and 70 are made. First exterior region 66 and second exterior region 70 may include porous metal material, such as Trabecular Metal™, comprising securement features, and exterior regions 74 and 78 may include flexible and/or elastic material designed to enable articulation of the joint. Exterior region 66, 70 may be attached to less than all of the articular surface associated with the joint. In one embodiment, exterior region 66, 70 may be attached to less than 50% of the articular surface associated with the joint.

Interior portion 64 includes first interior region 82, second interior region 86, and interior regions 90 and 94 connecting interior regions 82 and 86. First interior region 82 has first interior surface 84, second interior region 86 has second interior surface 88, and interior regions 90 and 94 have interior surfaces 92 and 96 connecting first and second interior surfaces 84 and 88, respectively. Regions 74, 78, 90 and 94 may comprise elastic materials, such as thermoplastic polyurethanes, polyolefins, and other high strength elastomers or any others disclosed in this document, for providing joint interpositional device 100 with increased extensibility and range of motion. As shown in FIG. 4, first and second interior region 82, 86 may be substantially coterminous with first and second exterior region 66, 70. In one embodiment, as shown in FIG. 5, first and second interior regions may comprise a continuous cross-section. In another embodiment, the first and second interior regions may have larger or smaller surface areas than the surface areas comprised by the first and second exterior regions, respectively.

Referring to FIG. 5, yet another exemplary joint interpositional device is shown. Device 100 generally may include exterior portion 102 and interior or internal portion 104. In operation, device 100 is positioned between a first joint surface and a second joint surface and functions similarly to device 20, as described above with reference to FIG. 3. Exterior portion 102 includes first exterior region 106 and second exterior region 110. First exterior region 106 has first exterior surface 108 and second exterior region 110 has second exterior surface 112. In one embodiment, first exterior region 106 comprises a surface area smaller than the surface area of acetabulum surface 53, and second exterior region 110 comprises a surface area smaller than the surface area of the articulating surface of femoral head surface 54. In another embodiment, each of first and second exterior region 106, 110 comprise a surface area of less than about 2.0 squared-inches. In yet another embodiment, each of first and second exterior region 106, 110 comprise a surface area of less than about 1.0 squared-inches. Exterior region 106, 110 may be made of any of the materials previously disclosed, including fibrous polymeric materials and metal containing highly porous materials. Interior portion 104, although shown as a single material, may be any previously described interior portion. Any material described herein may comprise a combination of materials and layers of materials such as mono-, bi-, tri- and multi-layered structures.

Figure 6:
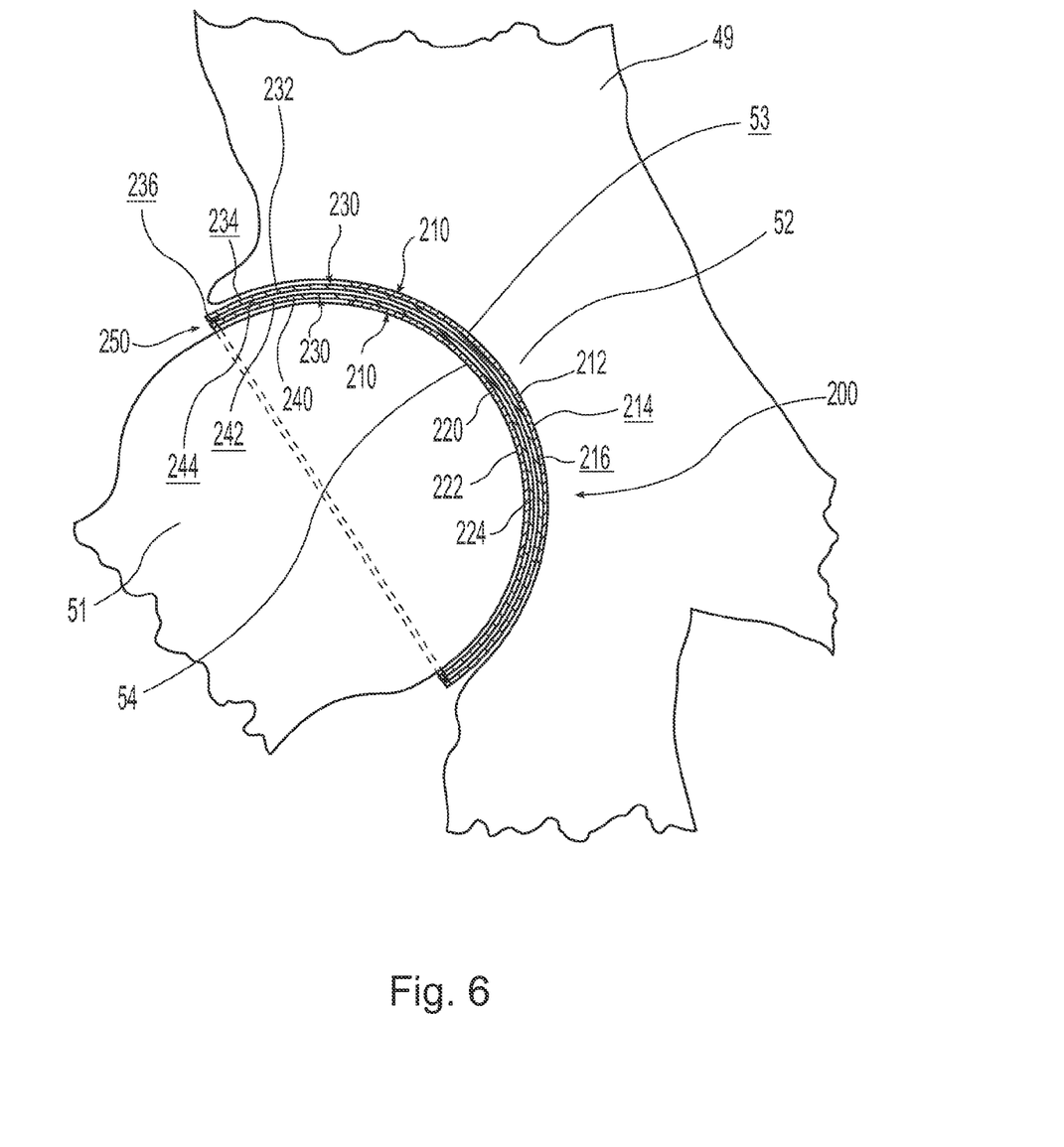
FIG. 6 is an anterior view of a femur and an acetabulum showing a cross-sectional view of another exemplary joint interpositional device positioned between the femur and the acetabulum.
Figure 7:
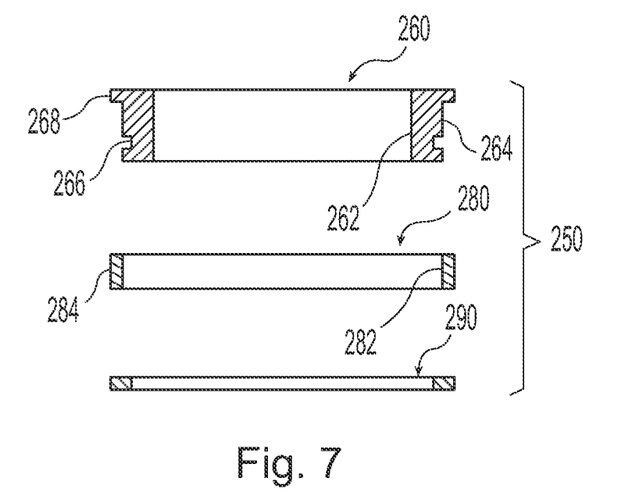
FIG. 7 is an exploded cross-sectional view of an internal rotational device showing an internal ring having an annular groove and a first lip, an external ring and a snap ring.
Figure 8:
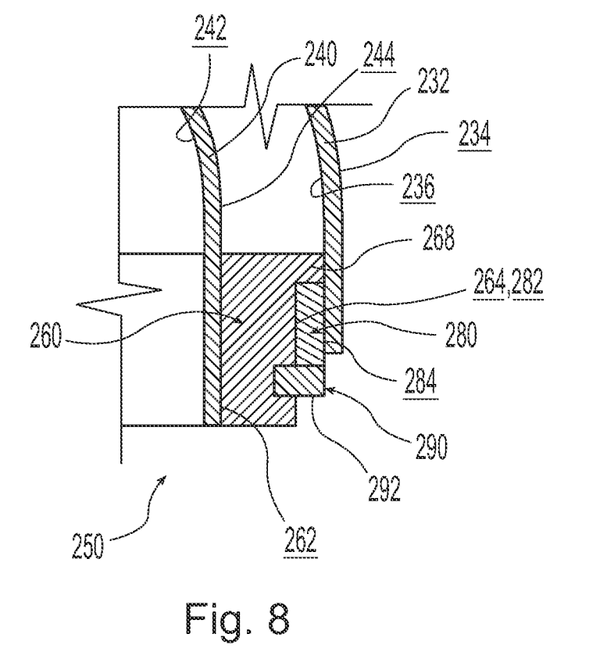
FIG. 8 is a partial cross-sectional view of the exemplary joint interpositional device of FIG. 6.

Referring to FIGS. 6-8, a further exemplary joint interpositional device is shown. Device 200 generally may include exterior portion 210, interior portion 230, and internal rotation device 250. In operation, device 200 is positioned between a first joint surface and a second joint surface and functions similarly to device 20, as described above with reference to FIG. 3. Exterior portion 210 has first external region 212 having surfaces 214 and 216 and second external region 220 having surfaces 222 and 224. Surfaces 214 and 222 attach to acetabular surface 53 and femoral head surface 54, respectively.

Interior portion 230 includes a first internal region 232 having surfaces 234 and 236 and a second internal region 240 having surfaces 242 and 244. Surfaces 236 and 244 attach to internal rotation device 250 as described in detail below with reference to FIG. 7. Portions of first and second internal regions 232 and 240 may extend beyond femoral head surface 54 and surround femoral head 51 such that internal rotation device 250, which is attached to first and second internal regions 232 and 240, will be positioned outside said joint. In other words, internal rotation device 250 is positioned outside said joint when it is not positioned between the natural articulating surfaces of the joint, e.g. femoral head surface 54 and acetabulum surface 53.

Internal rotation device 250 comprises two rotatably coupled rings having a common axis of rotation. The rings may be concentric or substantially concentric. In one embodiment, rotation device 250 comprises internal ring 260, external ring 280, and snap ring 290. Internal ring 260 comprises internal surface 262 and external surface 264. Internal surface 262 may be attached to surface 244 of second interior portion 240. External surface 264 has a profile including annular groove 266 and first lip 268. Snap ring 290 is partially positioned in annular groove 266 thereby creating second lip 292. External ring 280 has internal surface 282 and external surface 284. Internal surface 282 fits snugly over external surface 264 of internal ring 260 to contain wear or debris particles without creating an interference fit. First lip 268 and second lip 292 keep external ring 280 positioned on internal ring 260 and enable external ring 280 to rotate about internal ring 260. The clearance between internal ring 260 and external ring 280 which creates the snug fit will depend on the materials selected for construction of internal ring 260 and external ring 280 and processing tolerances. The snug fit of ring 260, 280 and the profile of surface 264 create an axial-radial path and an encapsulated body for containing debris particles.

External surface 284 of external ring 280 may be attached to surface 236 of first interior portion 232. Internal rotation device 250 provides means for rotating first interior portion 232 about second interior portion 240 along the common axis. First interior portion 232 may be attached to other surfaces of external ring 280 and that second interior portion 240 may be attached to other surfaces of internal ring 260. Furthermore, internal ring 260 and external ring 280 may be constructed, for example, of ceramic, metal, and polymer materials, and their surfaces may be coated to reduce their coefficients of friction. Polymeric rings may be flexible. According to one method of positioning device 200 in the joint, internal and external ring 260, 280 may be deformed and inserted between the natural articulating surfaces of a partially distracted joint. The rings may be configured to provide a rotatable coupling without requiring a snap ring by using different materials and surface profiles. While the rotatable coupling provides rotation about the axis of the rings, articulation in other directions is facilitated by use of elastic and/or flexible materials in portions of device 200 such as, for example, first interior portion 232 and second interior portion 240 as described in detail above.

Figure 9:
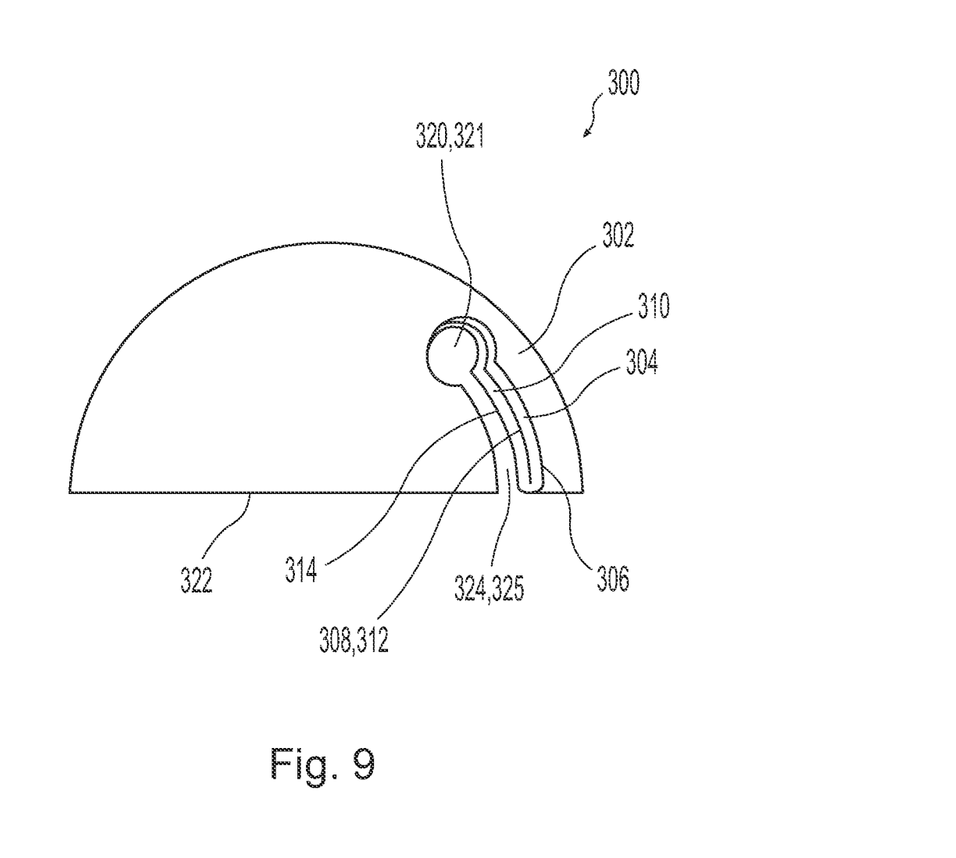
FIG. 9 is a partial perspective view of another exemplary joint interpositional device including a slit.
Figure 10:
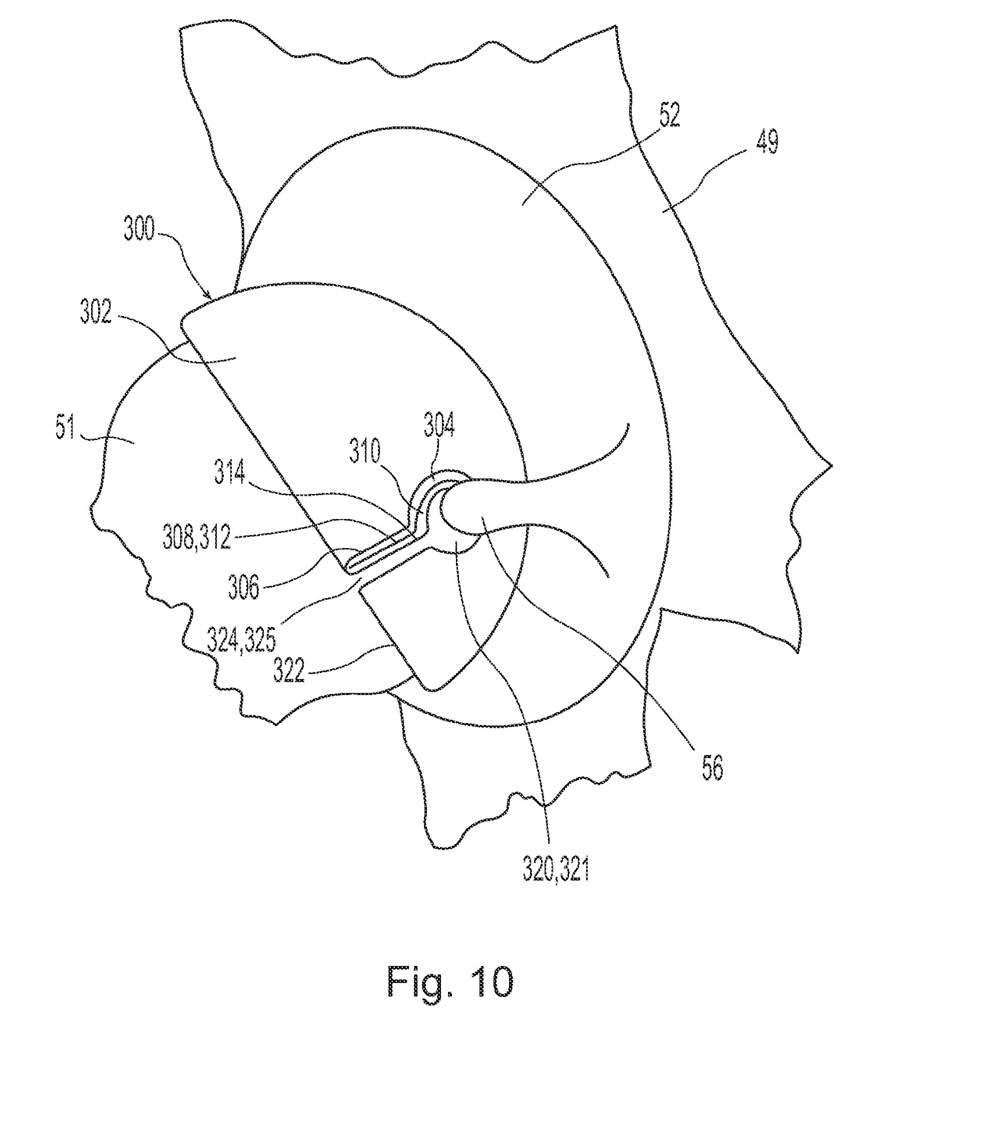
FIG. 10 is an anterior view of a femur and an acetabulum showing a side-view of the joint interpositional device of FIG. 9 positioned between the femur and the acetabulum.

Referring to FIGS. 9 and 10, another exemplary joint interpositional device is shown. Device 300 generally may comprise an exterior portion (not shown) including bone securement features and interior portion 302. Interior portion 302 includes first interior region 304 having surface 306, 308, second interior region 310 having surface 312, 314 and slit 324, 325 for positioning and retaining therein a ligament spanning the first and second joint surfaces, i.e., femoral head surface 54 and acetabulum surface 53. Optionally, interior portion 302 may include hole 320, 321 surrounding one end of slit 324, 325. Interior region 304 connects to interior region 310 at edge 22. Hole 320 extends from surface 306 to surface 308 of first interior region 304, and hole 321 extends from surface 312 to surface 314 of second interior region 310. Slit 324, 325 traverses first and second interior region 304, 310 from the axis of hole 320, 321 to edge 322. Surface 308, 312 comprises the articulation or bearing surface of device 300. Surface 308 may be sealed to surface 312 along the edge of slit 324, 325 and hole 320, 321 to form an encapsulated body for containing debris. The exterior portion may be any one of the exterior portions previously described with the addition, in some embodiments, of slits and holes corresponding to slit 324, 325 and hole 320, 321. In operation, device 300 is positioned between femoral head 51 and acetabulum 52. Slit 324, 325 is moved by ligamentum teres femoris 56 from edge 322 to hole 320, 321 until ligamentum teres femoris 56 seats in hole 320, 321, as shown in FIG. 10. Alternatively, slit 324, 325 may be sufficiently wide to encompass the periphery of hole 320, 321 such that ligamentum teres femoris 56 seats therein. FIG. 10 shows device 300 positioned generally on femoral head 51. Slit 324, 325, while shown to be substantially longitudinal, may also be curved and may originate at any point along edge 322.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. An interpositional prosthetic device for positioning between a first joint surface and a second joint surface of a joint, comprising:
   a first prosthetic component including a first external region and a first internal region, said first external region having a first bone securement feature, said first internal region having a first articulation surface, and said first prosthetic component being sized and shaped to be positioned over a first natural articular surface associated with the first joint surface;
   a second prosthetic component coupled to said first prosthetic component, said second prosthetic component including a second external region and a second internal region, said second external region having a second bone securement feature, said second internal region having a second articulation surface, and said second prosthetic component being sized and shaped to be positioned over a second natural articular surface associated with the second joint surface,
   wherein said first internal region and said second internal region cooperate to form an encapsulated body for containing debris produced from articulation between said first internal region and said second internal region;
   a first ring attached to said first prosthetic component; and
   a second ring attached to said second prosthetic component, said first ring rotatably contacting said second ring to rotatably couple said first prosthetic component and said second prosthetic component.

2. The interpositional prosthetic device of claim 1, wherein said first internal region is porous and has an average pore size smaller than about 0.2 μm.

3. The interpositional prosthetic device of claim 1, wherein said first bone securement feature comprises bone growth factors.

4. The interpositional prosthetic device of claim 1, wherein said first bone securement feature comprises tissue ingrowth material.

5. The interpositional prosthetic device of claim 1, wherein said first bone securement feature comprises biological material.

6. The interpositional prosthetic device of claim 1, wherein said first bone securement feature comprises a textured metal structure.

7. The interpositional prosthetic device of claim 6, wherein said first bone securement feature comprises a porous metal structure.

8. The interpositional prosthetic device of claim 1, wherein said first external region comprises a fibrous structure.

9. The interpositional prosthetic device of claim 1, wherein said joint comprises a first bone having said first natural articular surface and a second bone having said second natural articular surface, wherein said first ring and said second ring are adapted to be positioned outside the joint and surrounding a portion of said second bone.

10. The interpositional prosthetic device of claim 1, wherein said first prosthetic component and said second prosthetic component are flexible.

11. The interpositional prosthetic device of claim 1, wherein said first internal region is porous and an external average pore size of the first external region is larger than an internal average pore size of the first internal region.

12. The interpositional prosthetic device of claim 1, wherein said first ring and said second ring rotate about a common axis of rotation.

13. The interpositional prosthetic device of claim 1, wherein said first ring is attached to said first internal region and said second ring is attached to said second internal region.

14. The interpositional prosthetic device of claim 1, wherein said first ring and said second ring are deformable to position said interpositional prosthetic device in said joint when said joint is only partially distracted.

15. An interpositional prosthetic device for positioning between a first joint surface and a second joint surface of a joint, comprising:
- a first prosthetic component including first securement means for securing said first prosthetic component to the first joint surface, said first prosthetic component being sized and shaped to be positioned over the first joint surface;
- a second prosthetic component including second securement means for securing said second prosthetic component to the second joint surface, said second prosthetic component being sized and shaped to be positioned over the second joint surface;
- containment means for containing debris produced from articulation between said first prosthetic component and said second prosthetic component;
- a first ring attached to said first prosthetic component; and
- a second ring attached to said second prosthetic component, said first ring rotatably contacting said second ring to rotatably couple said first prosthetic component and said second prosthetic component.

16. The interpositional prosthetic device of claim 15, wherein said joint comprises a first bone having said first joint surface and a second bone having said second joint surface, wherein said first ring and said second ring are adapted to be positioned outside the joint and surrounding a portion of said second bone.

17. The interpositional prosthetic device of claim 15, wherein said containment means is porous and has an average pore size smaller than about 0.2 μm.

18. The interpositional prosthetic device of claim 15, wherein said first securement means comprises bone growth factors.

19. The interpositional prosthetic device of claim 15, wherein said first securement means comprises tissue ingrowth material.

20. The interpositional prosthetic device of claim 15, wherein said first securement means comprises biological material.

21. The interpositional prosthetic device of claim 15, wherein said first securement means comprises a textured metal structure.

22. The interpositional prosthetic device of claim 21, wherein said first securement means comprises a porous metal structure.

23. The interpositional prosthetic device of claim 15, wherein said first securement means comprises a fibrous construct.

24. An interpositional prosthetic device for positioning between a first joint surface and a second joint surface of a joint, the interpositional prosthetic device comprising:
- a first prosthetic component including a first external region and a first internal region, said first external region having a first bone securement feature, said first internal region having a first articulation surface, and said first prosthetic component being sized and shaped to be positioned over a natural articular surface associated with the first joint surface;
- a second prosthetic component coupled to said first prosthetic component, said second prosthetic component including a second external region and a second internal region, said second external region having a second bone securement feature, said second internal region having a second articulation surface, and said second prosthetic component being sized and shaped to be positioned over a natural articular surface associated with the second joint surface;
- a first ring attached to said first prosthetic component; and
- a second ring attached to said second prosthetic component, said first ring and said second ring rotatably coupling said first prosthetic component and said second prosthetic component, at least a portion of said first ring extending into a volume defined by said second ring.

25. The interpositional prosthetic device of claim 24, further including a third ring coupling the first ring and the second ring.

26. An interpositional prosthetic device for positioning between a first joint surface and a second joint surface of a joint, the interpositional prosthetic device comprising:
- a first prosthetic component including a first external region and a first internal region, said first external region having a first bone securement feature, said first internal region having a first articulation surface, and said first prosthetic component being sized and shaped to be positioned over a natural articular surface associated with the first joint surface;
- a second prosthetic component coupled to said first prosthetic component, said second prosthetic component including a second external region and a second internal region, said second external region having a second bone securement feature, said second internal region having a second articulation surface, and said second prosthetic component being sized and shaped to be positioned over a natural articular surface associated with the second joint surface;
- a first ring attached to said first prosthetic component, wherein at least said first ring, said first internal region and said second internal region form an encapsulating body having an enclosed encapsulating surface which contains debris produced from articulation between said first internal region and said second internal region, said enclosed encapsulating surface including encapsulating body facing surfaces of said first ring, said first internal region and said second internal region; and a second ring attached to said second prosthetic component, said first ring rotatably contacting said second ring to rotatably couple said first prosthetic component and said second prosthetic component.

27. The interpositional prosthetic device of claim 26, wherein said first ring and said second ring rotate about a single axis of rotation.

\* \* \* \* \*